United States Patent [19]
Holung

[11] Patent Number: 5,447,072
[45] Date of Patent: Sep. 5, 1995

[54] TORSIONAL TESTER FOR CIRCUIT CARDS

[75] Inventor: Joseph A. Holung, Royal Palm Beach, Fla.

[73] Assignee: International Business Machines Corporation, Armonk, N.Y.

[21] Appl. No.: 280,904

[22] Filed: Jul. 27, 1994

[51] Int. Cl.[6] ............................................. G01N 3/22
[52] U.S. Cl. ..................................... 73/848; 73/853; 73/854
[58] Field of Search ................. 73/847, 848, 849, 851, 73/853, 854, 856, 865.9

[56] References Cited

U.S. PATENT DOCUMENTS

| | | | |
|---|---|---|---|
| 4,958,522 | 9/1990 | McKinlay | 73/847 |
| 5,174,160 | 12/1992 | Morita et al. | 73/847 |

FOREIGN PATENT DOCUMENTS 0836692  6/1981  U.S.S.R. ................. 73/847

OTHER PUBLICATIONS

PCMCIA PC Card Standard, Release 2.0, Sep., 1991, Personal Computer Memory Card International Association, Sunnyvale, Calif., pp. 3-12, 3-24.

*Primary Examiner*—Richard E. Chilcot, Jr.
*Assistant Examiner*—Elizabeth L. Dougherty
*Attorney, Agent, or Firm*—Martin J. McKinley; Ronald V. Davidge

[57] ABSTRACT

A torsional tester includes test stations for one or more circuit cards. In each test station, one end of the circuit card under test is held stationary while the opposite end is twisted in a card holder mounted to pivot about an axis, being alternately driven by each of a pair of weights extending downward on a flexible member from opposite sides of a pulley. A rocker providing a platform extending under each of these weights is driven in a reciprocating pivoting motion in which the weights are alternately lifted and allowed to fall. The weight which is allowed to fall provides a torque to the pulley, while the weight being lifted does not provide such a torque. A pair of setscrews limits the angular motion of the card holder to a predetermined level in each direction.

10 Claims, 3 Drawing Sheets

TORSIONAL TESTER FOR CIRCUIT CARDS

BACKGROUND OF THE INVENTION

Field of the Invention

This invention relates to a fixture for applying mechanical tests to electronic circuit cards, and, more particularly, to a fixture for applying a torsional test specified by the PCMCIA to circuit cards otherwise built to PCMCIA specifications.

Background Information

The PCMCIA (Personal Computer Memory Card International Association) has developed a number of standards describing the characteristics of certain cards to be used in portable personal computers. These cards, which are usually called "PCMCIA cards," are removably mounted in standard slots to provide, for example, electronic memory or input/output adapter circuit functions. While each card has the length and width of a typical credit card, several different thicknesses of cards are used.

A portable personal computer configured to accept circuit cards of this type includes one or more specific slots into which a card can be manually slid. At the inner end of the slot, a connector, of a type also specified by PCMCIA standards, has a number of pins which engage receptacles extending along the inner end of the card. An ejection button adjacent to the slot aids in the removal of a card fully installed within the slot by pushing the card outward far enough to allow the card to be manually grabbed and slid outward. Electrical and mechanical characteristics of these circuit cards, and of connectors and devices configured to accept them, have been standardized to allow a typical slot within a computing device to accept a number of different cards, which may be examples of several different types of cards. This kind of flexibility allows programs stored on various cards to be loaded into a portable personal computer with the cards being alternately installed in a slot provided for the purpose. Also, the input/output capabilities of a portable personal computer to be reconfigured by changing cards having, for example, adapter circuits supporting fax/modem or printer functions.

Because circuit cards built to PCMCIA standards are used to increase the flexibility of portable computing equipment, and because such cards must often be repeatedly inserted and removed from the equipment, various mechanical stresses are placed on the cards, both during the card insertion and removal processes, and in the general handling encountered as the cards are carried from one place to another. Circuit cards are known to be susceptible to damage resulting from the application of mechanical stresses, particularly when torsion or flexure of a card results in bending stresses which may fracture circuit traces extending along the card and solder connections connecting the terminals of components attached to the card with these circuit traces.

To provide for the production of reliable circuit cards of this type, it is desirable to test card assemblies, with components attached by soldering, for operating characteristics after the application of mechanical stress patterns. While it is not necessary to test all of the cards produced by a manufacturing process in this way, it is particularly useful to apply this type of testing to various samples during the development of a card configuration and of a process for manufacturing a particular type of card. When testing is applied in this way, the card configuration or the manufacturing process can be altered to prevent damage caused by the application of stresses. It is also advisable to repeat testing of this kind to card samples selected during the manufacturing process, in order to determine whether changes adversely affecting the ability of the card to resist mechanical damage have occurred.

To facilitate this kind of testing, the PCMCIA organization has published a number of physical tests which circuit cards are expected to pass as part of their standard requirements. An example of these test requirements is the Torque Test listed at 3.6.2.16 of the PCMCIA PC Card Standard, Release 2.0, September, 1991, page 3–12 and 3–24. In this test, one end of the test card is clamped, and a torque in a first direction is applied to the other end of the card, at a level of 11 inch-lb (12.6 kg-cm), or at a level sufficient to cause a torsional deflection of the card through a 10-degree angle, whichever of these torque levels occurs first. After this torque is held on the card for five minutes, it is removed from the card, and a similar torque is applied to the card in the opposite direction for five minutes. This test is repeated at least five times in each direction. After the card is mechanically stressed in this way, it is examined and rejected if visible damage has occurred. Functional tests are applied to the card to determine whether the card functions as specified, and, if the card contains non-volatile memory, this memory is read to determine if the memory has retained data stored before the test.

A particular problem with this type of testing is associated with the time required for its completion, with torsional forces being applied to an individual card for about an hour. While a number of automated methods available to automate and accelerate functional circuit testing, the application of mechanical loads cannot be accelerated without departing from the requirements of the test. Thus, what is needed is an automated way to apply these stress levels, simultaneously to a number of cards being tested, without a requirement for human intervention as the direction in which torque is applied is reversed. Furthermore, an automated method for applying torque should operate as required by the test standard, applying torque to deflect the card through a specified angle, or the applying a specified torque level, whichever occurs first.

SUMMARY OF THE INVENTION

In accordance with one aspect of the invention, there is provided a device for applying a torque test to a circuit card, in which the device includes first and second card holding mechanisms, a drive mechanism, and a rotation limiting mechanism. The first card holding mechanism holds a first end of the card to prevent rotation of the first end. The second card holding mechanism, which is mounted to pivot about an axis, engages a second end of the card to apply rotation to the second end. The drive mechanism applies a constant torque about the axis to the second card holding mechanism. The rotation limiting mechanism stops motion of the second card holding mechanism after a predetermined angular motion has occurred.

BRIEF DESCRIPTION OF THE DRAWINGS

One preferred embodiment of the subject invention is hereafter described with specific reference being made to the following Figures, in which.

DETAILED DESCRIPTION

Figure 1:
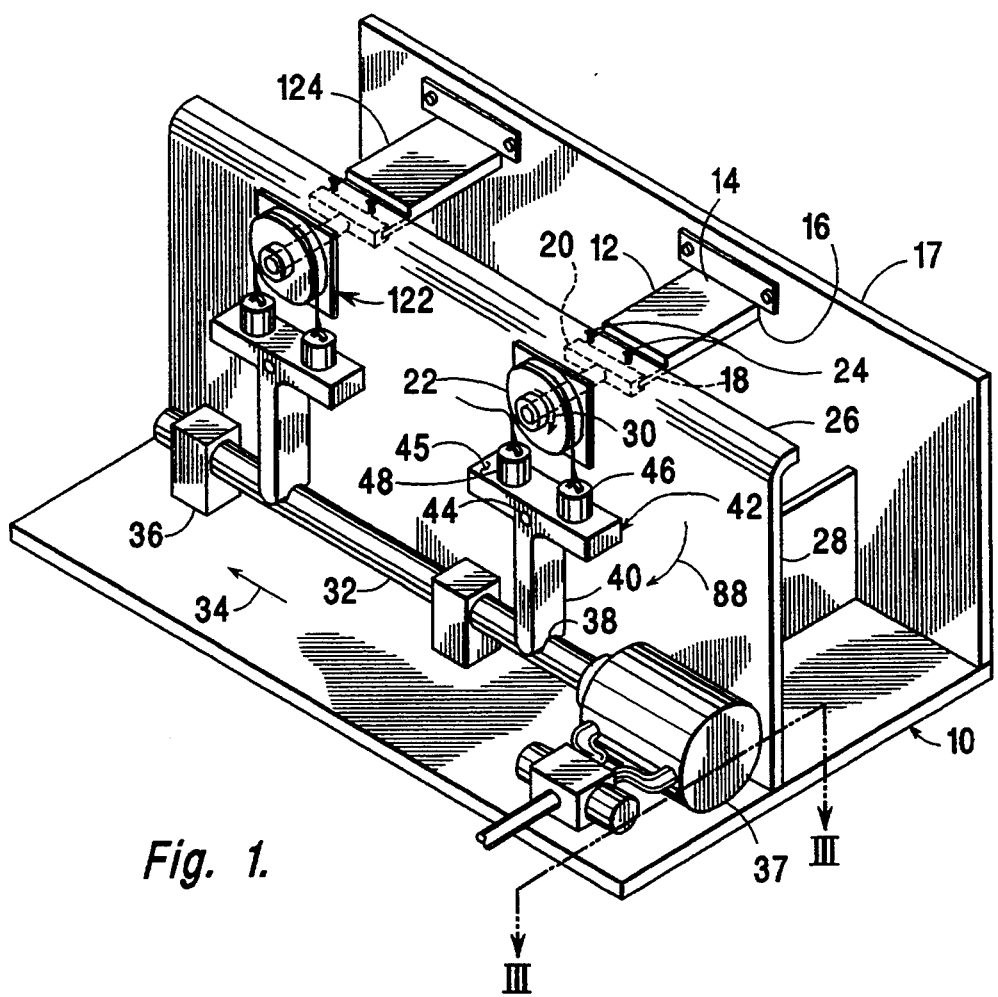
FIG. 1 is an isometric view of a torsional tester for circuit cards as viewed from above, to the front, and to the right.

FIG. 1 is an isometric view of a torsional tester 10, in which two circuit cards 12 are fastened for testing. Each test card 12 is clamped at a first end 14 within a stationary clamping slot 16 in a rear frame plate 17, and at a second end 18 within a pivoting clamping block 20, which is constrained to turn with a pulley 22.. A pair of set screws 24, extending downward from an upper flange 26 of front frame plate 28 limit the angular motion of pivoting clamping block 20 from a horizontal position (in which it is shown), in the direction of arrow 30 and opposite this direction. At the limit of this motion in each direction, an end of pivoting clamping block 20 comes into contact with a tip of a corresponding set screw 24 extending downward. For example, set screws 24 may be adjusted to allow ten degrees of angular motion in each direction, as required in the PCMCIA torsional test described above in the background of this invention.

The pivoting motion of each pulley 22 is initiated by sliding motion of rod 32 in the direction of arrow 34 and opposite this direction. Rod 32, which is mounted to slide in a pair of bearing blocks 36 as a pneumatic cylinder 37 is operated, includes a pair of upward-facing notches 38, each of which imparts motion to the tip of an arm 40 descending as part of a rocker 42. Each rocker 42, which is pivotally mounted on a shoulder screw 44 fastened to front frame plate 28, includes a platform surface 45, on which a pair of weights 46 and 48 are placed. These weights 46 and 48 are connected to opposite ends of a flexible member 50, which may be, for example, a bead chain.

Figure 2:
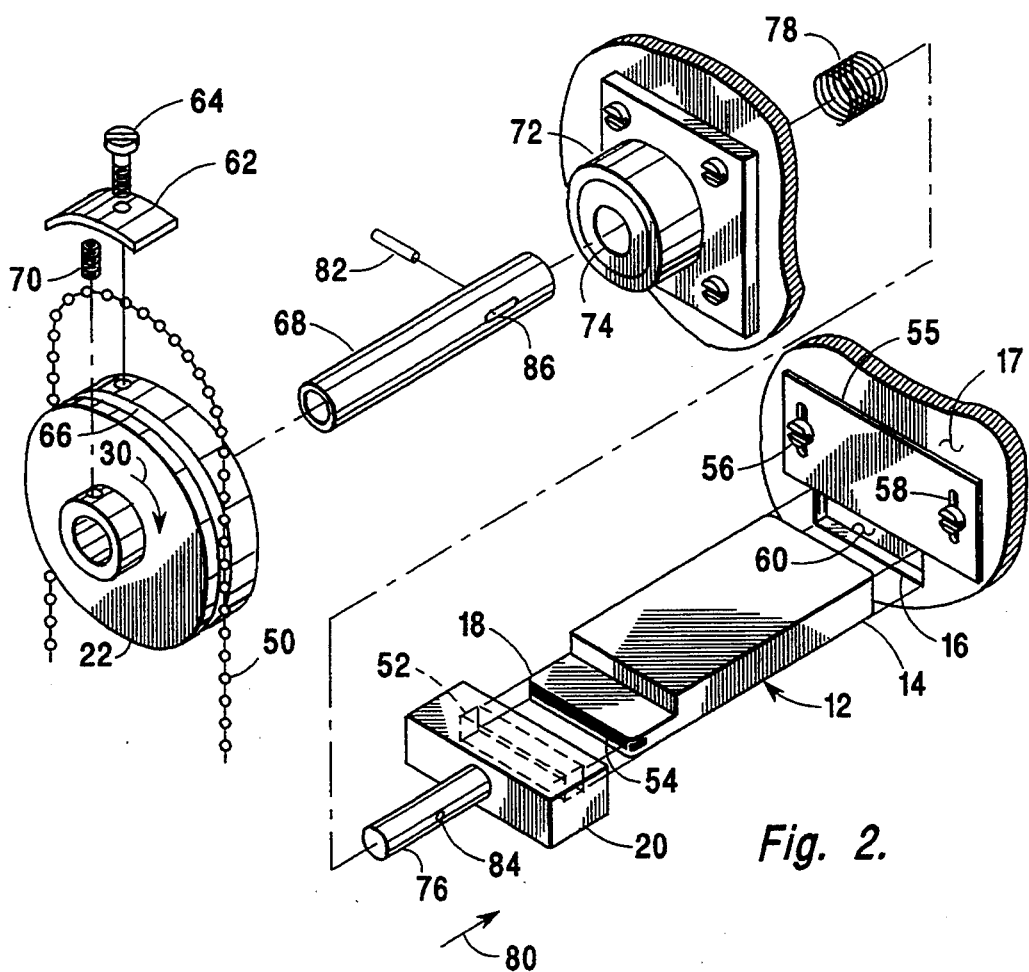
FIG. 2 is an exploded isometric view of a circuit card under test and the fixtures used to apply torsional loading to the card in the tester of FIG. 1, as viewed in FIG. 1.

FIG. 2 is an exploded isometric view of a circuit card under test and the fixtures used to apply torsional loading to the card in the tester of FIG. 1. As previously described in reference to FIG. 1, a first end 14 of test card 12 extends into a stationary clamping slot 16 within rear frame plate 17, while a second end 18 of card 12 extends into a cavity 52 within pivoting clamping block 20. A typical test card 12, built in accordance with PCMCIA standards, includes a second end 18 having a single thickness specified to assure engagement with a standard connector. A number of contact receptacles extend within individual apertures aligned in two rows along an end surface 54. First end 14 may have one of several different thicknesses specified in PCMCIA standards. To accommodate this allowed variation, an adjustable plate 55 establishes the effective thickness of stationary clamping slot 16. Each plate 55 is vertically movable, being held in place by a pair of screws 56 extending through slots 58 to be fastened into rear frame plate 17. A rear surface 60 of clamping slot 16 limits the motion of card end 14 into the slot 16. For example, this arrangement can be used to ensure that the maximum clamping length requirement of 0.5 inch (12.7 mm), specified in the PCMCIA test requirements referenced in the background of this invention, is maintained.

Continuing to refer to FIG. 2, Bead chain 50 is fastened to pulley 22 by a clamp 62 held in place using a screw 64. As pulley 22 rotates in the direction of arrow 30 and opposite this direction, bead chain 50 wraps and unwraps within groove 66 in pulley 22. Pulley 22 is fastened to a hollow shaft 68 by means of a set screw 70. Hollow shaft 68 is pivotally mounted to front frame plate 28 by means of a bearing block 72, which preferably includes a pair of ball bearings 74. A pivot shaft 76, attached to clamping block 20, extends into hollow shaft 68, while a compression spring 78 over shaft 68 pushes clamping block 20 in the direction of arrow 80 to engage second end 18 of card 12. A dowel pin 82 fits tightly through a hole 84 in pivot shaft 76 and loosely through slots 86 in hollow shaft 68. In this way, pivot shaft 84 is allowed to slide through the distance provided by slots 86, while being held in the direction of arrow 80 by compression spring 78, and while being constrained to turn with pulley 22. Thus, card 12 may be installed into the test fixture 10 and removed therefrom as the pivoting clamping block 20 is held in the direction opposite arrow 80 to provide the necessary clearance between clamping block 20 and clamping slot 16.

Referring again to FIG. 1, when rod 32 is moved in the direction of arrow 34, each rocker 42 is rotated in the direction of arrow 88, lifting weight 48 while the other weight 46 is allowed to fall. The radius of groove 66 (shown in FIG. 2) and the weight of each weight 46 and 48 may be chosen, for example, to provide the 11 in-lb (12.6 kg-cm) test torque specified by the PCMCIA standard identified in the background of this invention. A torque applied in this way by one of the weights 46 or 48 is resisted by the structure of the card 12 being tested. If the card 12 is stiff enough to resist this torque without deflecting through the maximum angle established by the set screws 24, the card remains twisted through the angle established by the torque. If the card 12 is not stiff enough to resist the torque applied by one of the weights 46 or 48 without deflecting through the maximum angle, the card remains twisted through the maximum angle.

The distance through which rod 32 is moved is sufficient to move each weight 46 or 48 upward enough to slacken the portion of bead chain 50 above the weight being lifted as the other weight is allowed to fall through the distance corresponding to the maximum distance allowed by the corresponding set screw 24. Thus, during the motion of pulley 22 in each direction through the maximum angle allowed by the set screws 24, one of the weights 46 or 48 is lifted, slackening the bead chain above the weight being lifted while the platform 44 is moved away from the other weight, allowing it to fall freely. In this way, only the force of a single weight is allowed to establish the torque transmitted by pulley 22 to the test card 12.

Figure 3:
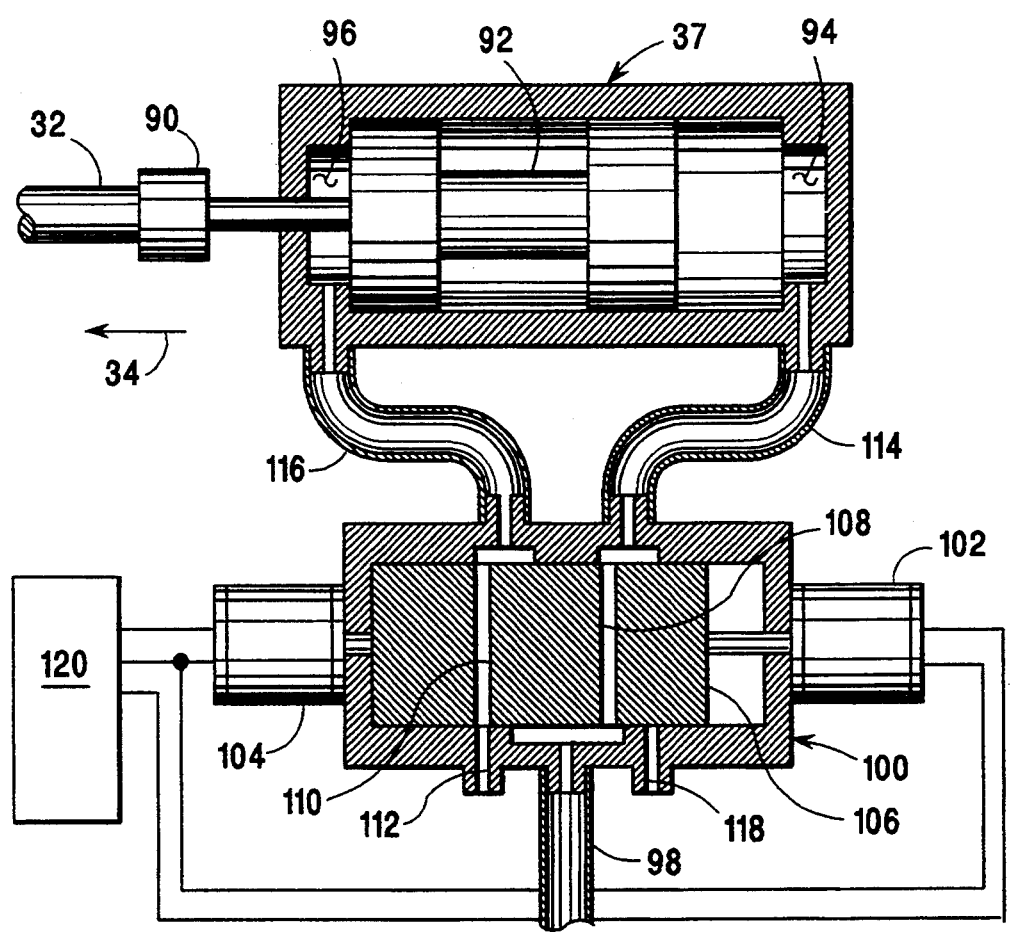
FIG. 3 is a horizontal cross-sectional view a pneumatic cylinder and valve assembly used to control the operation of the torsional tester of FIG. 1, taken as indicated by section lines III—III in FIG. 1.

FIG. 3 is a horizontal cross-sectional view of the apparatus used to control the movement of rod 32, taken as indicated by section lines III—III in FIG. 1. Rod 32 is connected to a pneumatic cylinder 37 by means of a coupling 90. Pneumatic cylinder 37 is of a double-acting type, with an internal piston 92 being driven in the direction of arrow 34 as air under pressure is introduced into a first chamber 94, and with the piston 92 being driven in the direction opposite arrow 34 as air under pressure is introduced into a second chamber 96.

Air to drive piston 92 is supplied from an external pressurized air source connected by a pipe 98 through a pneumatic valve 100 to cylinder 37. This valve 100 is in turn controlled by a pair of solenoids 102 and 104, which move a slider 106 within valve 100 in the direction of 34 and opposite this direction. Specifically, when solenoid 104 is energized with solenoid 102 turned off, slider 106 is pulled in the direction of arrow 34, so that a first passage 108 within slider 106 is brought into communication with air supply pipe 98, and so that a second passage 110 within slider 106 is brought into communication with an exhaust port 112. With slider 106 in this position, as it is shown in FIG. 3, air is supplied to first chamber 94 through a first connecting pipe 114 and exhausted from second chamber 96 through a second connecting pipe 116, causing piston 92 and rod 32 to move in the direction of arrow 34. Conversely, when solenoid 102 is energized with solenoid turned off, slider 106 is pulled in the direction opposite arrow 34, so that first passage 108 is brought into communication with exhaust port 118, and so that second passage 110 is brought into communication with air supply pipe 98. In this way, air is supplied to second chamber 96 and exhausted from first chamber 94, so piston 92 and rod 32 move opposite the direction of arrow 34.

The operation of solenoid valves 102 and 104 is in turn controlled by an electronic controller 120, which may constructed in one of many conventional ways for the purpose. The controller 120 has a capabilities of operating the solenoids 102 and 104 in alternating fashion, with each solenoid being left on for a predetermined time as required to execute the test, and of terminating the test after a prescribed number of solenoid cycles. This type of control may be built, for example, around a digital computer programmed to operate the solenoids in the desired sequence for the desired time periods, or a simple timing device using cams driven by a motor may be employed. Controller 120 preferably also includes means to terminate the testing when the desired number of cycles is completed and to alert the test operator that a time for replacing the cards has been reached.

Referring again to FIG. 1, a second test station 122 is provided to allow the simultaneous testing of a second card 124. Since an independent set of weights 46 and 48 is used to apply torque to each card, the tests are independent; the angle through which each card is deflected does not affect the testing of the other card. While two test stations are shown as an example, It is understood that this invention can be applied to a device having a single test station or to a device having a large number of test stations, each of which is driven by the reciprocating motion of rod 32 and pneumatic cylinder 37.

While the invention has been described in a particular embodiment applying the PCMCIA torque test to a circuit card, it is understood that a number of different embodiments within the scope of the invention can be configured to perform other particular tests. For example, a single weight can readily be used to apply a torque in one direction between cycles in which the card is returned to an undeflected condition.

While the invention has been described in its preferred form or embodiment with some degree of particularity, it is understood that this description has been given only by way of example and that numerous changes in the details of construction, fabrication and use, including the combination and arrangement of parts, may be made without departing from the spirit and scope of the invention.

What is claimed is:

1. Apparatus for applying a torque test to a circuit card, wherein said apparatus comprises:
    first card holding means for holding a first end of said card in a manner preventing rotation of said first end;
    second card holding means, mounted to pivot about an axis, for engaging a second end of said card in a manner applying rotation to said second end;
    drive means applying a constant torque about said axis to said second card holding means, wherein said drive means includes a pulley connected to said second card holding means, and a flexible member extending partly around an outer surface of said pulley, said flexible member being clamped to wrap and unwrap along said outer surface, with a first end portion of said flexible member hanging downward from a first side of said pulley, and with a second end portion of said flexible member hanging downward from a side of said pulley opposite said first side thereof, wherein said drive means additionally includes a first weight attached to said first end portion of said flexible member, a second weight attached to said second end portion of said flexible member, a first platform extending under said first weight, a second platform extending under said second weight, and platform drive means moving said first and second platforms in reciprocating motions, wherein said first platform is moved downward, out of contact with said first weight, and said second platform is moved upward in contact with said second weight, to apply a torque to said pulley in a first direction, and wherein said second platform is moved downward, out of contact with said second weight, and said first platform is moved upward in contact with said first weight, to apply a torque to said pulley opposite said first direction; and
    rotation limiting means stopping motion of said second card holding means after a predetermined angular motion has occurred.

2. The apparatus of claim 1:
    wherein said first and second platforms are formed as portions of a rocker, extending in opposite directions from a pivot point at which said rocker is pivotally mounted; and
    wherein said platform drive means includes rocker drive means moving said rocker in a reciprocating angular motion.

3. The apparatus of claim 2, wherein said rocker drive means includes:
    a drive arm extending as a portion of said rocker;
    a slidably mounted rod engaging said drive arm; and
    rod drive means for moving said rod in a reciprocating linear motion.

4. The apparatus of claim 3, wherein said rod drive means includes:
    a pressurized air source;
    a pneumatic cylinder having a first cavity at a first end, a second cavity at an end opposite said first end, a piston extending between said first and second cavities to be moved in alternating directions by air introduced into said first and second cavities;
    a valve pneumatically connected to said first and second cavities, including a valve structure movable by solenoid means between a first position, in which a first pressurizing path is opened, connecting said first cavity with said pressurized air source, and in which a first exhaust path is opened, connecting said second cavity with a first exhaust port, and a second position, in which a second pressurizing path is opened, connecting said second cavity with said pressurized air source, and in which a second exhaust path is opened, connecting said first cavity with a second exhaust port; and control means driving said solenoid means to operate in a preferred sequence.

5. Apparatus for applying a torque test to a circuit card, wherein said apparatus comprises:

first card holding means for holding a first end of said card in a manner preventing rotation of said first end, wherein said first card holding means includes a stationary card holding cavity and a plate covering a portion of said card holding cavity, and wherein said plate is movable along said cavity;

second card holding means, mounted to pivot about an axis, for engaging a second end of said card in a manner applying rotation to said second end;

drive means applying a constant torque about said axis to said second card holding means; and rotation limiting means stopping motion of said second card holding means after a predetermined angular motion has occurred.

6. Apparatus for applying a torque test to a circuit card, wherein said apparatus comprises:

first card holding means for holding a first end of said card in a manner preventing rotation of said first end;

second card holding means, mounted to pivot about an axis, for engaging a second end of said card in a manner applying rotation to said second end, and wherein said second card holding means is mounted to slide along said axis to disengage said second end;

drive means applying a constant torque about said axis to said second card holding means; and rotation limiting means stopping motion of said second card holding means after a predetermined angular motion has occurred.

7. Apparatus for simultaneously applying a torque test to a plurality of circuit cards, wherein said apparatus comprises:

a plurality of first card holders, wherein each of said first card holders holds a first end of a said circuit card in a manner preventing rotation of said first end;

a plurality of second card holders, wherein each of said second card holders engages a second end of a said card in a manner applying rotation to said second end, wherein each of said second card holders is mounted to pivot about an axis extending opposite an associated one of said first card holders;

a movable drive member driven in a reciprocating motion; and motion transfer means imparting rotary motion to each of said second card holders, wherein said rotary motion is derived from said reciprocating motion of said movable member, wherein said motion transfer means applies a constant torque to each of said second card holders about a said axis thereof, wherein said motion transfer means stops motion of each of said second card holders after a predetermined angular motion has occurred, wherein said motion transfer means applies a first level of torque in a first angular direction to each of said plurality of second card holders and a second level of torque opposite said first direction to each of said plurality of second card holders, wherein said motion transfer means limits rotary motion of each of said plurality of second card holders about a said axis in each direction, wherein said motion transfer means includes a plurality of pulleys, with each pulley within said plurality of pulleys being connected to a second card holder within said plurality of second card holders, wherein said motion transfer means additionally includes a plurality of flexible members, with each flexible member within said plurality of flexible members extending partly around an outer surface of a pulley within said plurality of pulleys, with each said flexible member within said plurality of flexible members being clamped to wrap and unwrap along said outer surface, with a first end portion of said flexible member hanging downward from a first side of said pulley connected to a first weight, and with a second end portion of said flexible member hanging downward from a side of said pulley opposite said first side thereof connected to a second weight; and wherein said motion transfer means additionally includes a plurality of rockers, with each said rocker being mounted to pivot about a central point below a pulley within said plurality of pulleys, with each said rocker including a first platform extending under said first weight connected to said pulley above said rocker, with each said rocker including a second platform extending under said second weight connected to said pulley above said rocker; and with each said rocker including a drive arm extending to engage said movable drive member.

8. The apparatus of claim 7, wherein said movable drive member is driven by drive means including:

a pressurized air source;

a pneumatic cylinder having a first cavity at a first end, a second cavity at an end opposite said first end, a piston extending between said first and second cavities to be moved in alternating directions by air introduced into said first and second cavities;

a valve pneumatically connected to said first and second cavities, including a valve structure movable by solenoid means between a first position, in which a first pressurizing path is opened, connecting said first cavity with said pressurized air source, and in which a first exhaust path is opened, connecting said second cavity with a first exhaust port, and a second position, in which a second pressurizing path is opened, connecting said second cavity with said pressurized air source, and in which a second exhaust path is opened, connecting said first cavity with a second exhaust port; and control means driving said solenoid means to operate in a preferred sequence.

9. Apparatus for simultaneously applying a torque test to a plurality of circuit cards, wherein said apparatus comprises:

a plurality of first card holders, wherein each of said first card holders holds a first end of a said circuit card in a manner preventing rotation of said first end, wherein each first card holder within said plurality of first card holders includes a stationary card holding cavity and a plate covering a portion of said card holding cavity, and wherein said plate is movable along said cavity;

a plurality of second card holders, wherein each of said second card holders engages a second end of a said card in a manner applying rotation to said second end, wherein each of said second card holders is mounted to pivot about an axis extending opposite an associated one of said first card holders;

a movable drive member driven in a reciprocating motion; and motion transfer means imparting rotary motion to each of said second card holders, wherein said rotary motion is derived from said reciprocating motion of said movable member, wherein said motion transfer means applies a constant torque to each of said second card holders about a said axis thereof, wherein said motion transfer means stops motion of each of said second card holders after a predetermined angular motion has occurred, wherein said motion transfer means applies a first level of torque in a first angular direction to each of said plurality of second card holders and a second level of torque opposite said first direction to each of said plurality of second card holders, and wherein said motion transfer means limits rotary motion of each of said plurality of second card holders about a said axis in each direction.

10. Apparatus for simultaneously applying a torque test to a plurality of circuit cards, wherein said apparatus comprises:

a plurality of first card holders, wherein each of said first card holders holds a first end of a said circuit card in a manner preventing rotation of said first end;

a plurality of second card holders, wherein each of said second card holders engages a second end of a said card in a manner applying rotation to said second end, wherein each of said second card holders is mounted to pivot about an axis extending opposite an associated one of said first card holders, and wherein each second card holder within said plurality of second card holders is mounted to slide along said axis thereof to disengage a said second end;

a movable drive member driven in a reciprocating motion; and motion transfer means imparting rotary motion to each of said second card holders, wherein said rotary motion is derived from said reciprocating motion of said movable member, wherein said motion transfer means applies a constant torque to each of said second card holders about a said axis thereof, wherein said motion transfer means stops motion of each of said second card holders after a predetermined angular motion has occurred, wherein said motion transfer means applies a first level of torque in a first angular direction to each of said plurality of second card holders and a second level of torque opposite said first direction to each of said plurality of second card holders, and wherein said motion transfer means limits rotary motion of each of said plurality of second card holders about a said axis in each direction.

* * * * *